(12) United States Patent
Banju et al.

(10) Patent No.: US 11,986,757 B2
(45) Date of Patent: May 21, 2024

(54) FILTRATION FILTER

(71) Applicant: Murata Manufacturing Co., Ltd., Nagaokakyo (JP)

(72) Inventors: Masaru Banju, Nagaokakyo (JP); Takashi Kondo, Nagaokakyo (JP); Shusuke Yokota, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 469 days.

(21) Appl. No.: 17/323,125

(22) Filed: May 18, 2021

(65) Prior Publication Data

US 2021/0268417 A1  Sep. 2, 2021

Related U.S. Application Data

(63) Continuation of application No. PCT/JP2019/050159, filed on Dec. 20, 2019.

(30) Foreign Application Priority Data

Jan. 7, 2019 (JP) ................................. 2019-000490

(51) Int. Cl.
*B01D 39/20* (2006.01)
*C12M 1/00* (2006.01)
*C12M 1/26* (2006.01)
*C23F 1/44* (2006.01)
*C25D 1/08* (2006.01)
(Continued)

(52) U.S. Cl.
CPC ......... *B01D 39/2027* (2013.01); *C12M 29/04* (2013.01); *C12M 33/14* (2013.01); *C12M 47/02* (2013.01); *C12M 47/12* (2013.01); *B01D 2239/10* (2013.01); *C23F 1/44* (2013.01); *C25D 1/08* (2013.01); *C25D 3/567* (2013.01); *C25D 5/022* (2013.01); *C25D 5/48* (2013.01)

(58) Field of Classification Search
None
See application file for complete search history.

(56) References Cited

U.S. PATENT DOCUMENTS

| 4,463,060 A * | 7/1984 | Updegraff ................ C25D 5/48 |
| | | 428/669 |
| 9,981,090 B2 | 5/2018 | Hogan |

(Continued)

FOREIGN PATENT DOCUMENTS

| CN | 106574291 A | 4/2017 |
| JP | 2015527481 A | 9/2015 |

(Continued)

OTHER PUBLICATIONS

Chinese Office Action issued for Chinese Patent Application No. 201980086078.0, dated Mar. 9, 2022.

(Continued)

*Primary Examiner* — Clare M Perrin
(74) *Attorney, Agent, or Firm* — Arentfox Schiff LLP

(57) ABSTRACT

A filtration filter according to the present invention includes a surface layer composed mainly of Pd, a base material inside the surface layer and composed mainly of a PdNi alloy, and an intermediate layer between the surface layer and the base material, wherein the intermediate layer is composed mainly of a PdNi alloy in which a Pd:Ni ratio changes from a surface layer side toward a base material side.

14 Claims, 13 Drawing Sheets

(51) Int. Cl.
  *C25D 3/56* (2006.01)
  *C25D 5/02* (2006.01)
  *C25D 5/48* (2006.01)

(56) References Cited

U.S. PATENT DOCUMENTS

| | | |
|---|---|---|
| 10,512,736 B2 | 12/2019 | Hogan |
| 10,632,753 B2 | 4/2020 | Niisato et al. |
| 2013/0334338 A1 | 12/2013 | Hogan |
| 2014/0299539 A1* | 10/2014 | Takai ............... B01D 39/10 210/506 |
| 2015/0101596 A1 | 4/2015 | Hogan |
| 2016/0136552 A1* | 5/2016 | Nakanishi ............ A61M 1/36 210/695 |
| 2017/0269086 A1 | 9/2017 | Takai et al. |
| 2018/0021708 A1 | 1/2018 | Takai et al. |
| 2018/0312803 A1* | 11/2018 | Banju ............. B01D 67/0062 |
| 2018/0353881 A1* | 12/2018 | Yamamoto ........... B01D 39/10 |
| 2019/0039374 A1 | 2/2019 | Higashibeppu |
| 2019/0193403 A1 | 6/2019 | Niisato et al. |
| 2020/0078536 A1 | 3/2020 | Hogan |

FOREIGN PATENT DOCUMENTS

| | | |
|---|---|---|
| JP | 2018088932 A | 6/2018 |
| JP | 2019116653 A | 7/2019 |
| WO | 2014162810 A1 | 10/2014 |
| WO | 2017131178 A1 | 8/2017 |

OTHER PUBLICATIONS

Written Opinion of the International Search Authority issued for PCT/JP2019/050159, dated Mar. 10, 2020.
International Search Report issued for PCT/JP2019/050159, dated Mar. 10, 2020.
Extended European Search Report issued for EP Application No. 19 90 8550, dated May 6, 2022.

* cited by examiner

| SAMPLE | CONDITIONS | COMPONENT RATIO (%) | |
|---|---|---|---|
| | | Ni | Pd |
| EXAMPLE 1 | BEFORE IMMERSED IN AQUEOUS ACETIC ACID HYDROGEN PEROXIDE | 7 | 93 |
| | AFTER IMMERSED IN AQUEOUS ACETIC ACID HYDROGEN PEROXIDE | 0 | 100 |

| SAMPLE | CONDITIONS | COMPONENT RATIO (%) | |
|---|---|---|---|
| | | Ni | Pd |
| EXAMPLE 2 | BEFORE IMMERSED IN AQUEOUS ACETIC ACID HYDROGEN PEROXIDE | 11 | 89 |
| | AFTER IMMERSED IN AQUEOUS ACETIC ACID HYDROGEN PEROXIDE | 0 | 100 |

| COMPOSITION OF PdNi PLATING FILM | Pd CONCENTRATION RATIO % | 52 | 58 | 66 | 68 | 80 |
|---|---|---|---|---|---|---|
| | Ni CONCENTRATION RATIO % | 48 | 42 | 34 | 32 | 20 |
| Ni RATIO OF SURFACE LAYER XPS (atomic%) | | ND | ND | ND | ND | ND |

ND: BELOW DETECTION LIMIT

FIG. 15

| IMMERSION TIME IN AQUEOUS ACETIC ACID HYDROGEN PEROXIDE | | 0 s | 10 s | 30 s | 1 min | 5 min | 30 min | 1 h | 2 h |
|---|---|---|---|---|---|---|---|---|---|
| COMPONENT RATIO OF SURFACE LAYER XPS (atomic%) | Ni | 10 % | 9 % | 9 % | 0 % | 0 % | 0 % | 0 % | 0 % |
| | Pd | 90 % | 91 % | 91% | 100 % | 100 % | 100 % | 100 % | 100 % |

FILTRATION FILTER

CROSS REFERENCE TO RELATED APPLICATIONS

The present application is a continuation of International application No. PCT/JP2019/050159, filed Dec. 20, 2019, which claims priority to Japanese Patent Application No. 2019-000490, filed Jan. 7, 2019, the entire contents of each of which are incorporated herein by reference.

FIELD OF THE INVENTION

The present invention relates to a filtration filter.

BACKGROUND OF THE INVENTION

For example, filters for trapping biological materials described in Patent Document 1 are known as filtration filters. In the filters described in Patent Document 1, a surface of a filter for trapping a biological material made of a metal other than gold is plated with gold, and the gold plating is electroless gold plating.

Patent Document 1: Japanese Unexamined Patent Application Publication No. 2018-88932

SUMMARY OF THE INVENTION

However, there is room for improvement in the corrosion resistance of the filters described in Patent Document 1.

It is an object of the present invention to provide a filtration filter with improved corrosion resistance.

A filtration filter according to one aspect of the present invention includes a surface layer composed mainly of Pd; a base material inside the surface layer and composed mainly of a PdNi alloy; and an intermediate layer between the surface layer and the base material, wherein the intermediate layer is composed mainly of a PdNi alloy in which a Pd:Ni ratio changes from a surface layer side toward a base material side.

The present invention can provide a filtration filter with improved corrosion resistance.

BRIEF DESCRIPTION OF THE DRAWINGS

FIG. 15 is a table of analysis results of a Ni component in a surface layer of a filtration filter in Example 7.

DETAILED DESCRIPTION OF THE PREFERRED EMBODIMENTS

Figure 1:
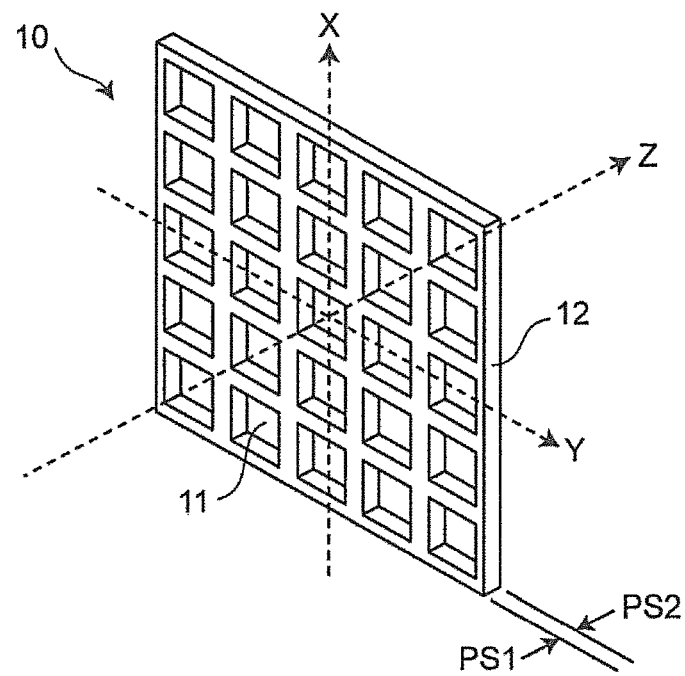
FIG. 1 is a schematic perspective view of a portion of an example of a filtration filter according to a first embodiment of the present invention.

Filtration filters for trapping biological materials are known (see Patent Document 1, for example). In such filtration filters, a surface of a base material formed of a non-precious metal is coated with a noble metal by plating or the like to form a surface layer of the noble metal on the surface of the base material of the non-precious metal. This reduces the dissolution of the base material when the filtration filter comes into contact with an electrolyte solution, such as physiological saline.

In such filtration filters, however, the surface layer on the base material may have a defect. For example, when an impurity adheres to the surface of the base material or when the base material has a large surface roughness, a coating material may not adhere to the defective portion, and the base material surface may be exposed through the defect. In such a case, there is a problem that the electrolyte solution comes into contact with the base material through the defect on the surface layer, and the base material is eluted through the defect.

When the base material of the non-precious metal is coated with a noble metal, a surface layer of the noble metal is formed on the surface of the base material such that the surface layer of the noble metal is laminated on the surface of the base material. Thus, a continuous interface is formed between the surface layer of the noble metal and the base material of the non-precious metal.

The present inventors have found a problem that when an electrolyte solution flows into a filtration filter through a defect on a surface layer, the surface layer and a base material come into contact with each other via the electrolyte solution and form a local cell at the interface therebetween, thus resulting in the corrosion of the base material.

More specifically, when a filtration filter including a base material of a non-precious metal coated with a noble metal comes into contact with an electrolyte solution, the electrolyte solution may flow into the filtration filter through a defect on the surface layer and may come into contact with the interface between the surface layer and the base material. Given this situation, a local cell is formed by the surface layer of the noble metal, the base material of the non-precious metal, and the electrolyte solution in contact with the interface between the surface layer and the base material. Consequently, an anodic reaction occurs on the surface of the base material of the non-precious metal, and the base material is corroded. The continuous interface facilitates the contact with the electrolyte solution flowing in through the defect on the surface layer and promotes corrosion. At the continuous interface, the corrosion of a portion of the base material spreads easily over the entire base material.

These problems make it difficult to improve the corrosion resistance of the filtration filter. Thus, the present inventors have completed the following invention by finding a filtration filter that includes an intermediate layer composed mainly of a PdNi alloy between a surface layer composed mainly of Pd and a base material composed mainly of a PdNi alloy, wherein the Pd:Ni ratio of the PdNi alloy of the intermediate layer changes.

A filtration filter according to one aspect of the present invention includes a surface layer composed mainly of Pd, a base material inside the surface layer and composed mainly of a PdNi alloy, and an intermediate layer between the surface layer and the base material, wherein the intermediate layer is composed mainly of a PdNi alloy in which a Pd:Ni ratio changes from a surface layer side toward a base material side. Such a structure can improve corrosion resistance.

The ratio of Ni to Pd in the intermediate layer preferably increases along the depth direction of the filtration filter. Such a structure can further improve corrosion resistance.

The intermediate layer may have a larger thickness than the surface layer. Such a structure can further improve corrosion resistance.

The intermediate layer may be formed in a region with a depth of more than 10 nm and 35 nm or less from a surface of the filtration filter. Such a structure can further improve corrosion resistance.

The base material may have a Pd:Ni ratio of 80:20, and the intermediate layer may have a Pd:Ni ratio varying in the range of 100:0 to 80:20. Such a structure can further improve corrosion resistance.

The base material may have a Pd:Ni ratio in the range of 75:25 to 85:15, and the intermediate layer may have a Pd:Ni ratio varying in the range of 100:0 to 75:25. Such a structure can further improve corrosion resistance.

A first embodiment of the present invention is described below with reference to the accompanying drawings. In the drawings, each component is exaggerated for convenience of description.

First Embodiment

[General Structure]

Figure 2:
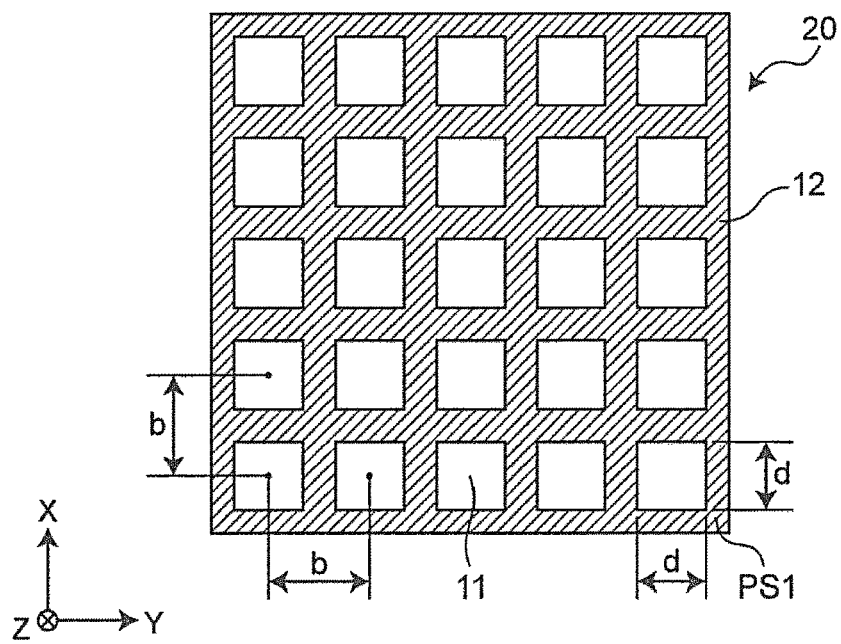
FIG. 2 is a schematic view of a portion of the filtration filter of FIG. 1 viewed in the thickness direction.

FIG. 1 is a schematic perspective view of a portion of an example of a filtration filter 10 according to a first embodiment of the present invention. FIG. 2 is a schematic view of a portion of the filtration filter 10 of FIG. 1 viewed in the thickness direction. The X, Y, and Z directions in the drawing indicate the vertical direction, the horizontal direction, and the thickness direction of the filtration filter 10, respectively. FIGS. 1 and 2 are enlarged views of a portion of the filtration filter 10.

As illustrated in FIGS. 1 and 2, the filtration filter 10 includes a filter base portion 12 with a plurality of through-holes 11. The filtration filter 10 is a plate-like structure that has a first main surface PS1 on which an object to be filtered contained in a liquid is trapped and a second main surface PS2 facing the first main surface PS1.

The term "object to be filtered", as used herein, refers to an object to be filtered among objects contained in a liquid. For example, an object to be filtered may be a biological substance contained in a liquid. The term "biological substance" refers to a substance originating from an organism, such as a cell (eukaryote), bacterium (*eubacterium*), or virus. Examples of the cell (eukaryote) include induced pluripotent stem cells (iPS cells), ES cells, stem cells, mesenchymal stem cells, mononuclear cells, single cells, cell clusters, suspension cells, adherent cells, neuronal cells, leukocytes, cells for regenerative medicine, autologous cells, cancer cells, circulating cancer cells (CTC), HL-60, HELA, and fungi. Examples of the bacterium (*eubacterium*) include *Escherichia coli* and *Mycobacterium tuberculosis*.

Examples of the "liquid" include electrolyte solutions, cell suspensions, and cell culture media.

The through-holes 11 in the filter base portion 12 are periodically arranged on the first main surface PS1 and the second main surface PS2 of the filtration filter 10. More specifically, the through-holes 11 are arranged in a matrix at regular intervals in the filter base portion 12.

In the first embodiment, the through-holes 11 have a square shape when viewed from the first main surface PS1 side of the filtration filter 10, that is, in the Z direction. The shape of the through-holes 11 viewed in the thickness direction of the filtration filter 10 (in the Z direction) is not limited to square and may be rectangular, polygonal, circular, or elliptical.

In the first embodiment, the through-holes 11 have a rectangular shape (cross-sectional shape) when projected onto a plane perpendicular to the first main surface PS1 of the filtration filter 10. More specifically, the length of one side of each through-hole 11 in the vertical direction (X direction) and the horizontal direction (Y direction) of the filtration filter 10 is larger than the depth of each through-hole 11 in the thickness direction (Z direction) of the filtration filter 10. The cross-sectional shape of the through-holes 11 is not limited to rectangular and may be a tapered shape, such as a parallelogram or trapezoid, a symmetric shape, or an asymmetric shape.

In the first embodiment, the through-holes 11 are arranged at regular intervals in two array directions parallel to each side of the square when viewed from the first main surface PS1 side of the filtration filter 10 (in the Z direction), that is, in the X direction and in the Y direction in FIG. 1. The through-holes 11 in the square lattice arrangement can have an increased opening ratio and can reduce the resistance of liquid passing through the filtration filter 10. Such a structure can shorten the filtration time and reduce stress on an object to be filtered.

The arrangement of the through-holes 11 is not limited to the square lattice arrangement and may be a quasi-periodic arrangement or a periodic arrangement. The periodic arrangement may be a square or rectangular arrangement, such as a rectangular arrangement with intervals different in two array directions, a triangular lattice arrangement, or a regular triangular lattice arrangement. The through-holes 11 may be arranged in any manner, provided that the filter base portion 12 has a plurality of through-holes 11.

The interval b between the through-holes 11 is appropriately determined according to the type (size, form, property, elasticity) or number of cells to be filtered. As illustrated in FIG. 2, the interval b between the through-holes 11 refers to the distance between the center of a through-hole 11 and the center of an adjacent through-hole 11 when the through-holes 11 are viewed from the first main surface PS1 side of the filtration filter 10. In the periodic arrangement structure, the interval b between the through-holes 11 may be more than one time and not more than 10 times the length of one side d of the through-holes 11, preferably not more than three times the length of one side d of the through-holes 11. The filtration filter 10 may have an opening ratio of 10% or more, preferably 25% or more. Such a structure can reduce the resistance of liquid passing through the filtration filter 10. This can shorten the processing time and reduce stress on cells. The opening ratio is calculated by (the area occupied by the through-holes 11)/(the projected area of the first main surface PS1 in the absence of the through-holes 11).

The filtration filter 10 preferably has a thickness of more than 0.1 times and not more than 100 times the size (one side d) of the through-holes 11. More preferably, the filtration filter 10 has a thickness of more than 0.5 times and not more than 10 times the size (one side d) of the through-holes 11. Such a structure can reduce the resistance of the filtration filter 10 to liquid and shorten the filtration time. This can reduce stress on an object to be filtered.

In the filtration filter 10, the first main surface PS1 with which a liquid containing an object to be filtered comes into contact preferably has a small surface roughness. The surface roughness refers to the average difference between the maximum value and the minimum value measured with a stylus profilometer at five points on the first main surface PS1. In the first embodiment, the surface roughness is preferably smaller than the size of an object to be filtered and is more preferably smaller than half the size of the object to be filtered. In other words, the openings of the through-holes 11 on the first main surface PS1 of the filtration filter 10 are formed on one plane (XY plane). The filter base portion 12, which is a portion where the through-holes 11 are not formed, is continuous and is formed in one piece. Such a structure can reduce the adhesion of an object to be filtered to the surface (first main surface PS1) of the filtration filter 10 and can reduce the resistance of liquid.

In the through-holes 11, the openings on the first main surface PS1 communicate with the openings on the second main surface PS2 through a continuous wall surface. More specifically, in the through-holes 11, the openings on the first main surface PS1 can be projected onto the openings on the second main surface PS2. In other words, when the filtration filter 10 is viewed from the first main surface PS1 side, in the through-holes 11, the openings on the first main surface PS1 overlap the openings on the second main surface PS2. In the first embodiment, the inner wall of each through-hole 11 is perpendicular to the first main surface PS1 and the second main surface PS2.

Figure 3:
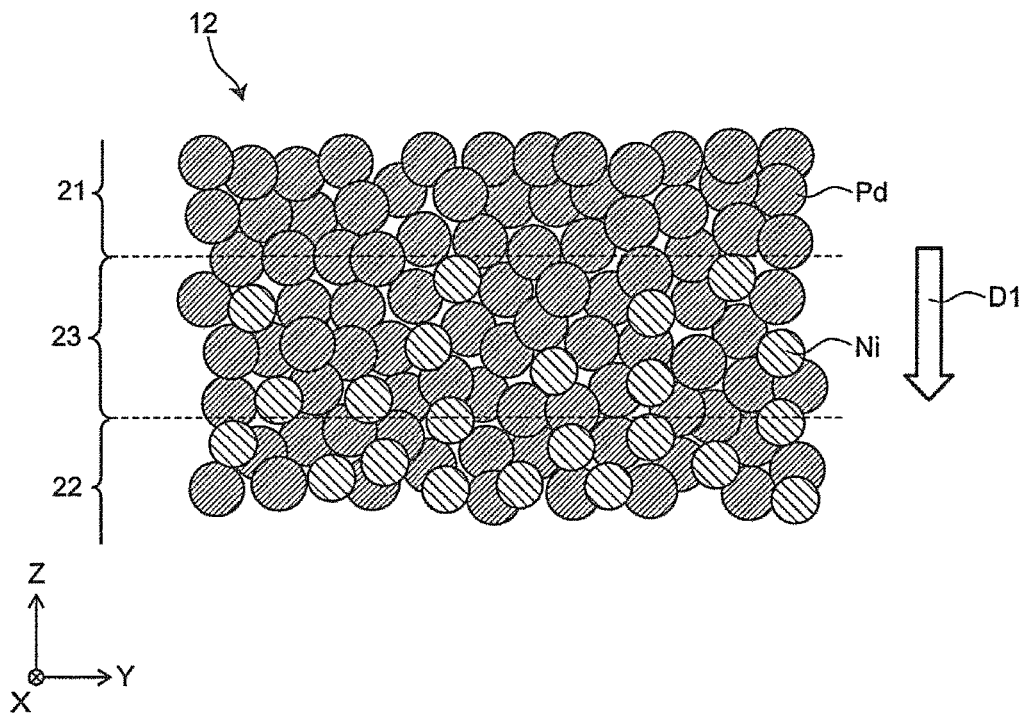
FIG. 3 is a schematic view of a portion of an example of the filtration filter according to the first embodiment of the present invention.

FIG. 3 is a schematic view of a portion of an example of the filtration filter 10 according to the first embodiment of the present invention. FIG. 3 illustrates a portion of an example of the filter base portion 12. As illustrated in FIG. 3, the filter base portion 12 includes a surface layer 21, a base material 22 inside the surface layer 21, and an intermediate layer 23 between the surface layer 21 and the base material 22. The surface layer 21 is composed mainly of Pd. The base material 22 is composed mainly of a PdNi alloy. The intermediate layer 23 is composed mainly of a PdNi alloy in which the Pd:Ni ratio changes from the surface layer 21 side toward the base material 22 side.

In the surface layer 21, "composed mainly of Pd" means that the number percentage of Pd atoms in the surface layer 21 is more than 90%. In the base material 22, "composed mainly of a PdNi alloy" means that the number percentage of Pd atoms in the base material 22 is 70% or more. In the intermediate layer 23, "composed mainly of a PdNi alloy" means that the number percentage of Pd atoms in the intermediate layer 23 is 50% or more.

The "PdNi alloy in which the Pd:Ni ratio changes" refers to a PdNi alloy in which the Pd content and the Ni content change stepwise or continuously in the depth direction D1 of the filtration filter 10. For example, a change in the Pd:Ni ratio is measured by secondary ion mass spectrometry (SIMS). The Pd:Ni ratio can be measured by component analysis performed by SIMS at a predetermined pitch in the depth direction D1 from the surface of the filtration filter 10.

The surface layer 21 may contain a component other than Pd. For example, the surface layer 21 may contain Au, Pt, Fe, Cu, Ti, C, and an oxide thereof. The base material 22 and the intermediate layer 23 may contain a component other than PdNi. For example, the base material 22 and the intermediate layer 23 may contain Au, Pt, Fe, Cu, Ti, Co, Mo, C, and an oxide thereof.

The surface layer 21 is a layer on the surface of the filtration filter 10. The surface layer 21 covers the base material 22 with the intermediate layer 23 interposed therebetween. The surface layer 21 is composed mainly of Pd and does not contain Ni. Thus, the surface layer 21 has a Pd:Ni ratio of 100:0.

The base material 22 is a main material of the filtration filter 10 and is covered with the surface layer 21 with the intermediate layer 23 interposed therebetween. The base material 22 is composed mainly of a PdNi alloy with a constant Pd:Ni ratio. The base material 22 has a larger thickness than the surface layer 21 and the intermediate layer 23. The base material 22 has a Pd:Ni ratio in the range of 75:25 to 85:15. In the first embodiment, the PdNi alloy of the base material 22 has a Pd:Ni ratio of 80:20.

The intermediate layer 23 is a layer between the surface layer 21 and the base material 22. The intermediate layer 23 is composed mainly of a PdNi alloy in which the Pd:Ni ratio changes. In the intermediate layer 23, the Pd:Ni ratio changes in the depth direction D1 of the filtration filter 10. More specifically, in the intermediate layer 23, the ratio of Ni to Pd of the PdNi alloy increases from the surface layer 21 toward the base material 22. The Pd:Ni ratio of the intermediate layer 23 changes in the range of 100:0 to 75:25 in the depth direction D1 of the filtration filter 10. In the first embodiment, the Pd:Ni ratio of the intermediate layer 23 changes from 100:0 to 80:20 as the depth increases in the depth direction D1 of the filtration filter 10.

In the intermediate layer 23, Ni is dispersed. Thus, in the intermediate layer 23, the interface between Pd and Ni is not continuous and is dispersed.

The intermediate layer 23 has a larger thickness than the surface layer 21. Thus, the interface between Pd and Ni is easily dispersed in the thickness direction of the filtration filter 10 (in the Z direction). This can reduce corrosion at the interface between Pd and Ni.

[One Example of Production Method]

An example of a method for producing the filtration filter 10 is described with reference to FIGS. 4A to 4G. FIGS. 4A to 4G illustrate an example of a production process of the filtration filter 10 according to the first embodiment of the present invention.

Figure 4A:
FIG. 4A is a schematic view of an example of a production process of the filtration filter according to the first embodiment of the present invention.

As illustrated in FIG. 4A, a substrate 31 made of silicon or the like is prepared. The substrate 31 may be subjected to surface cleaning, for example.

Figure 4B:
FIG. 4B is a schematic view of an example of a production process of the filtration filter according to the first embodiment of the present invention.

As illustrated in FIG. 4B, a Cu film 32 500 nm in thickness is formed on the substrate 31. For example, the Cu film 32 is formed by sputtering with a sputter deposition apparatus. Alternatively, the Cu film 32 may be formed by vapor deposition with a vapor deposition apparatus. To improve the adhesion between the substrate 31 and the Cu film 32, a Ti film 50 nm in thickness may be formed between the substrate 31 and the Cu film 32.

Figure 4C:
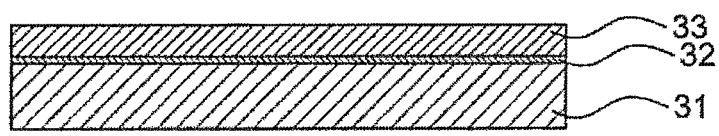
FIG. 4C is a schematic view of an example of a production process of the filtration filter according to the first embodiment of the present invention.

As illustrated in FIG. 4C, a resist is applied to the Cu film 32 and is dried to form a resist film 33 2 μm in thickness. For example, a photosensitive positive liquid resist (Pfi-3A manufactured by Sumitomo Chemical Co., Ltd.) is applied to the Cu film 32 with a spin coater. The spin coater conditions include 1140 rpm and 30 seconds, for example. Next, the resist is heated and dried on a hot plate to form the resist film 33 2.0 μm in thickness. The hot plate conditions include a heating temperature of 90° C. and a heating time of 90 seconds, for example.

Figure 4D:
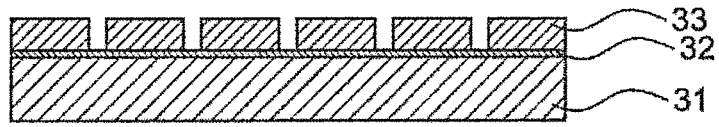
FIG. 4D is a schematic view of an example of a production process of the filtration filter according to the first embodiment of the present invention.

As illustrated in FIG. 4D, the resist film 33 is exposed to light and is developed to remove a portion of the resist film 33 corresponding to the filter base portion 12. For example, an i-line stepper (Pfi-37A manufactured by Canon Inc.) is used as an exposure apparatus. Development is performed with a paddle developing apparatus. Tetramethylammonium hydroxide (TMAH) is used as a developer. Exposure to light and development are followed by washing with water and drying.

Figure 4E:
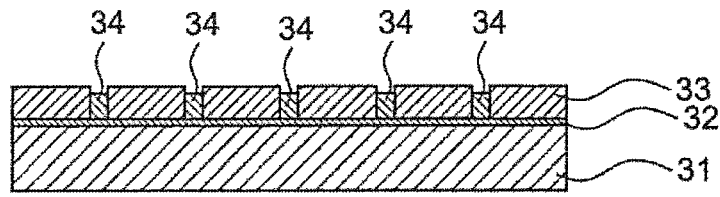
FIG. 4E is a schematic view of an example of a production process of the filtration filter according to the first embodiment of the present invention.

As illustrated in FIG. 4E, electroplating is performed in a PdNi plating bath with an electroplating apparatus. Thus, a PdNi plating film 34 is formed on the portion from which the resist film 33 has been removed. The electroplating conditions include a current density of 1 $A/dm^2$, an electric quantity of 4 AM, a pH of the plating solution of 7.5, and a plating thickness of 1.6 μm, for example.

Figure 4F:
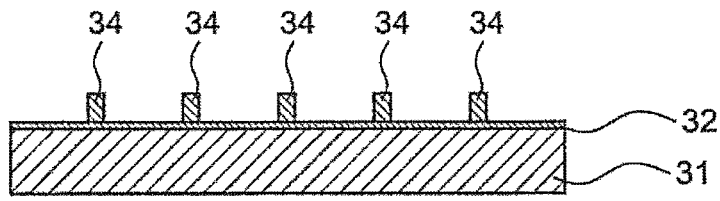
FIG. 4F is a schematic view of an example of a production process of the filtration filter according to the first embodiment of the present invention.

As illustrated in FIG. 4F, the resist film 33 is stripped with a stripping liquid NMP (N-methyl-2-pyrrolidone) in a resist stripping apparatus capable of high-pressure spray treatment. Subsequently, the PdNi plating film 34 is washed with IPA (isopropyl alcohol), is washed with water, and is dried.

Figure 4G:
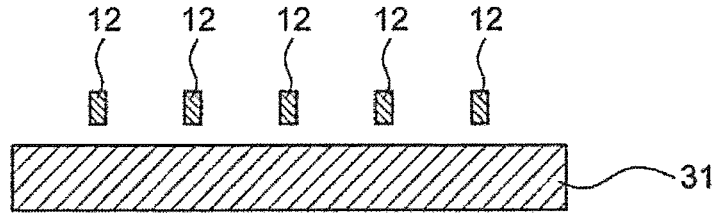
FIG. 4G is a schematic view of an example of a production process of the filtration filter according to the first embodiment of the present invention.

As illustrated in FIG. 4G, aqueous acetic acid hydrogen peroxide (acetic acid:hydrogen peroxide:water=5:5:90, room temperature) is prepared as an etchant and as a liquid for dissolving and removing Ni from the surface layer of the PdNi plating film 34, and the Cu film 32 is etched by immersion treatment for 48 hours while stirring with a stirrer. Thus, the PdNi plating film 34 is removed from the substrate 31, and Ni in the surface layer of the PdNi plating film 34 is dissolved. Thus, the filter base portion 12 is formed.

The immersion treatment of the PdNi plating film 34 in the aqueous acetic acid hydrogen peroxide can gradually dissolve Ni from the surface of the PdNi plating film 34 toward the inside. In the vicinity of the surface of the PdNi plating film 34, Ni in the PdNi plating film 34 easily comes into contact with the aqueous acetic acid hydrogen peroxide and is easily dissolved. However, it becomes more difficult for Ni in the PdNi plating film 34 at a deeper position to come into contact with the aqueous acetic acid hydrogen peroxide and to dissolve. Thus, the amount of dissolved Ni decreases gradually from the surface of the PdNi plating film 34 toward the inside.

Thus, in the vicinity of the surface of the filter base portion 12, the aqueous acetic acid hydrogen peroxide dissolves Ni, and the surface layer 21 composed mainly of Pd is formed. The amount of Ni dissolved in the aqueous acetic acid hydrogen peroxide decreases gradually from the surface layer 21 of the filter base portion 12 in the depth direction D1. The intermediate layer 23 thus formed is composed mainly of a PdNi alloy in which the Pd:Ni ratio changes. Thus, a portion of the PdNi plating film 34 in which Ni is not dissolved in the aqueous acetic acid hydrogen peroxide becomes the base material 22.

It is possible in this way to produce the filtration filter 10, which includes the surface layer 21 composed mainly of Pd, the base material 22 composed mainly of a PdNi alloy, and the intermediate layer 23 composed mainly of a PdNi alloy in which the Pd:Ni ratio changes formed between the surface layer 21 and the base material 22.

Example 1

Example 1 is described below. In Example 1, a portion of the filter base portion 12 produced by the above production method was used as a sample, and the Pd:Ni ratio in the depth direction D1 of the filter base portion 12 was analyzed.

In Example 1, the PdNi plating film 34 with a Pd:Ni ratio of 80:20 was immersed in the aqueous acetic acid hydrogen peroxide to form the filter base portion 12.

Secondary ion mass spectrometry (SIMS) was used for the analysis. Analytical conditions are described below.

(Analytical Conditions)

Measuring apparatus: PHI ADEPT1010 (quadrupole secondary ion mass spectrometer), manufactured by ULVAC-PHI, Inc.

Primary ion species: $Cs^+$

Primary accelerating voltage: 5.0 kV

Detection area: 75 μm×75 μm

Elements to be analyzed: Pd, Ni

In the analysis, the outer surface of the filter base portion 12 was irradiated with primary ions. The surface at the position where the measuring apparatus detected the first metal information was assumed to have a depth of 0 nm. Thus, in Example 1, the surface with a depth of 0 nm is defined as the surface of the filter base portion 12.

Figure 5:
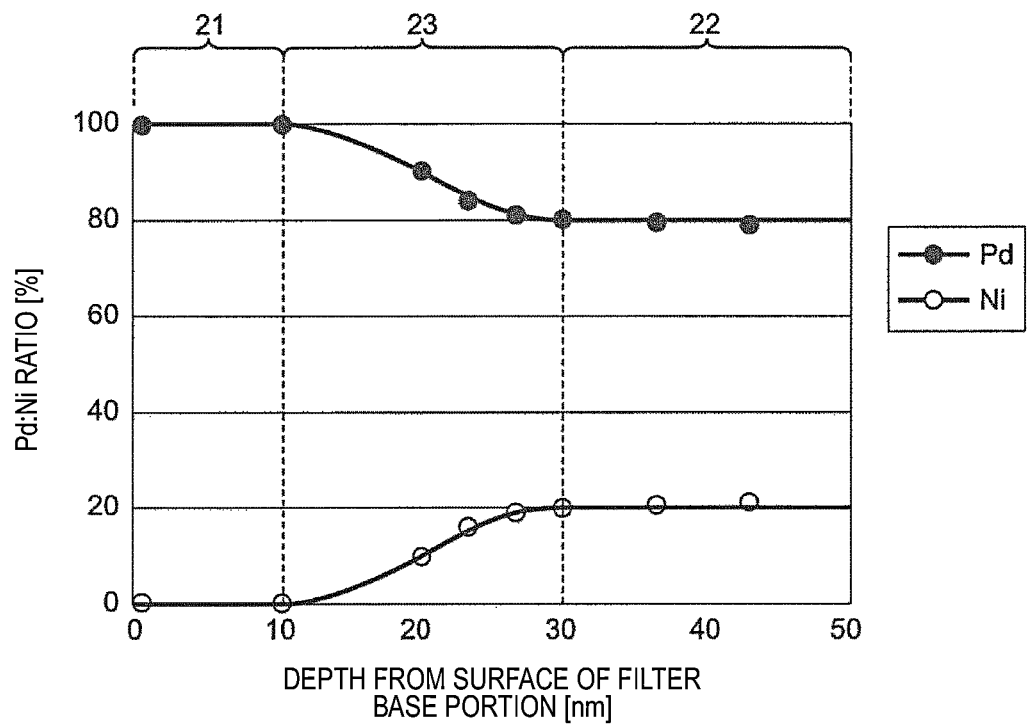
FIG. 5 is analytical data of the Pd:Ni ratio of a filter base portion of Example 1 in the depth direction.

FIG. 5 shows analytical data of the Pd:Ni ratio of the filter base portion 12 of Example 1 in the depth direction D1. As illustrated in FIG. 5, in Example 1, the surface layer 21 is formed in a region with a depth in the range of 0 to 10 nm from the surface of the filter base portion 12. Thus, the surface layer 21 has a thickness of 10 nm. In the surface layer 21, Pd constitutes 100%, and Ni constitutes 0%. Thus, the surface layer 21 has a Pd:Ni ratio of 100:0.

The intermediate layer 23 is formed in a region with a depth of more than 10 nm and 30 nm or less from the surface of the filter base portion 12. More preferably, the intermediate layer 23 is formed in a region with a depth in the range of 20 to 30 nm from the surface of the filtration filter 10. Thus, the intermediate layer 23 has a thickness in the range of 10 to 20 nm. In the intermediate layer 23, the Pd content decreases from 100% to 80%, and the Ni content increases from 0% to 20%. Thus, in the intermediate layer 23, the Pd:Ni ratio changes in the range of 100:0 to 80:20.

Although the intermediate layer 23 is formed in a region with a depth of more than 10 nm and 30 nm or less from the surface of the filter base portion 12 in Example 1, the region in which the intermediate layer 23 is formed is not limited to the region in Example 1. The intermediate layer 23 is formed at least in a region with a depth in the range of 20 to 30 nm from the surface of the filtration filter 10. For example, the intermediate layer 23 may be formed in a region with a depth of more than 10 nm and 40 nm or less from the surface of the filter base portion 12. The intermediate layer 23 may also be formed in a region with a depth of more than 10 nm and 35 nm or less from the surface of the filter base portion 12.

Thus, the ratio of Ni to Pd in the PdNi alloy in the intermediate layer 23 increases with the depth in the depth direction D1 of the filtration filter 10. In other words, the ratio of Ni to Pd in the PdNi alloy in the intermediate layer 23 increases from the surface layer 21 side toward the base material 22 side.

The base material 22 is formed in a region with a depth of more than 30 nm from the surface of the filter base portion 12. In the base material 22, Pd constitutes 80%, and Ni constitutes 20%. The base material 22 has a constant Pd:Ni ratio of 80:20.

Next, in Example 1, component analysis was performed on the surface of the filter base portion 12. The analysis was performed by X-ray photoelectron spectroscopy (XPS). Under analytical conditions, the analysis was performed on the surface of the PdNi plating film 34 before immersed in the aqueous acetic acid hydrogen peroxide (see FIG. 4F) and on the surface of the filter base portion 12 after immersed in the aqueous acetic acid hydrogen peroxide (see FIG. 4G).

Figures 6, 7, 8:
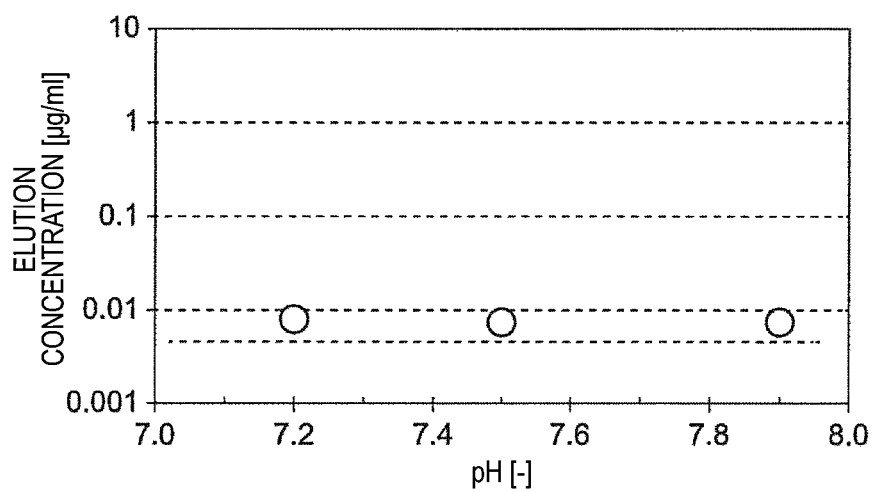
FIG. 6 is a table of component analysis results of a surface layer of the filter base portion of Example 1.
FIG. 7 is a table of component analysis results of a surface layer of a filter base portion of Example 2.
FIG. 8 is a graph of analysis results of the elution concentration of Ni in Example 3.

FIG. 6 is a table of component analysis results of the surface of the filter base portion 12 of Example 1. As shown in FIG. 6, in Example 1, the Ni content is 7% and the Pd content is 93% on the surface of the PdNi plating film 34 before immersed in the aqueous acetic acid hydrogen peroxide.

In Example 1, when the PdNi plating film 34 is immersed in the aqueous acetic acid hydrogen peroxide to form the filter base portion 12, the Ni content becomes 0% and the Pd content becomes 100% on the surface of the filter base portion 12.

The analysis results in Example 1 show that the PdNi plating film 34 can be immersed in the aqueous acetic acid hydrogen peroxide to remove Ni from the surface layer of the PdNi plating film 34. Thus, the filter base portion 12 including the surface layer 21 composed mainly of Pd could be produced.

Example 2

In Example 2, the filter base portion 12 was subjected to the component analysis at a Pd:Ni ratio different from the Pd:Ni ratio in Example 1. In Example 2, the PdNi plating film 34 with a Pd:Ni ratio of 50:50 was immersed in the aqueous acetic acid hydrogen peroxide to form the filter base portion 12. The analysis method and analytical conditions in Example 2 are the same as those in Example 1.

FIG. 7 is a table of component analysis results of the surface of the filter base portion 12 of Example 2. As shown in FIG. 7, in Example 2, the Ni content is 11% and the Pd content is 89% on the surface of the PdNi plating film 34 before immersed in the aqueous acetic acid hydrogen peroxide.

Also in Example 2, when the PdNi plating film 34 is immersed in the aqueous acetic acid hydrogen peroxide to form the filter base portion 12, the Ni content becomes 0% and the Pd content becomes 100% on the surface of the filter base portion 12.

The analysis results in Example 2 also show that the PdNi plating film 34 could be immersed in the aqueous acetic acid hydrogen peroxide to remove Ni from the surface layer of the PdNi plating film 34 and thereby produce the filter base portion 12 including the surface layer 21 composed mainly of Pd.

Example 3

Example 3 is described below. In Example 3, the filtration filter 10 was produced by the above production method at different pH values of the plating solution for the PdNi plating bath. The pH values of the plating solution were 7.2, 7.5, and 7.9. In Example 3, the filtration filter 10 was subjected to an elution test. In the elution test, a portion with a surface area of 1 cm 2 in the filtration filter 10 was immersed in 10 ml of PBS and was kept at 37° C. in an incubator for one week. The elution concentrations of Pd and Ni were analyzed with an ICP-MS (manufactured by Agilent Technologies). The detection limit of the ICP-MS for Pd and Ni is 0.005 μg/ml.

Figure 9:
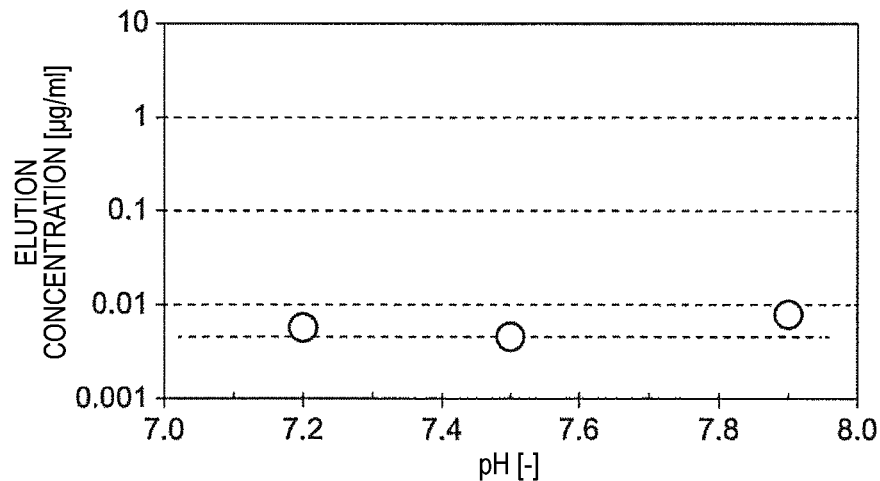
FIG. 9 is a graph of analysis results of the elution concentration of Pd in Example 3.

FIG. 8 is a graph of analysis results of the elution concentration of Ni in Example 3. FIG. 9 is a graph of analysis results of the elution concentration of Pd in Example 3. FIGS. 8 and 9 show that the elution concentrations of Pd and Ni were below the detection limit of the ICP-MS for Pd and Ni. This indicates that Pd and Ni are not eluted in Example 3.

Preferably, the pH value of the plating solution ranges from 7.0 to 8.5. More preferably, the pH value of the plating solution ranges from 7.2 to 7.9.

Example 4

Example 4 is described below. In Example 4, the filtration filter 10 was produced by the above production method at different current densities of the PdNi plating bath. The current densities ranged from 2.9 to 14.5 [A/dm$^2$]. In Example 4, the filtration filter 10 was subjected to an elution test. In the elution test, a portion with a surface area of 1 cm 2 in the filtration filter 10 was immersed in 10 ml of PBS and was kept at 37° C. in an incubator for one week. In the same manner as in Example 3, the elution concentrations of Pd and Ni were analyzed with the ICP-MS (manufactured by Agilent Technologies).

Figure 10:
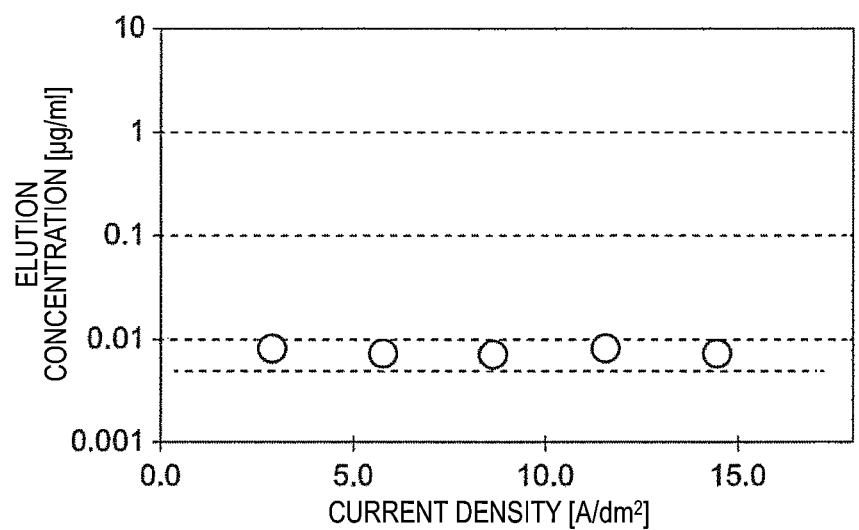
FIG. 10 is a graph of analysis results of the elution concentration of Ni in Example 4.
Figure 11:
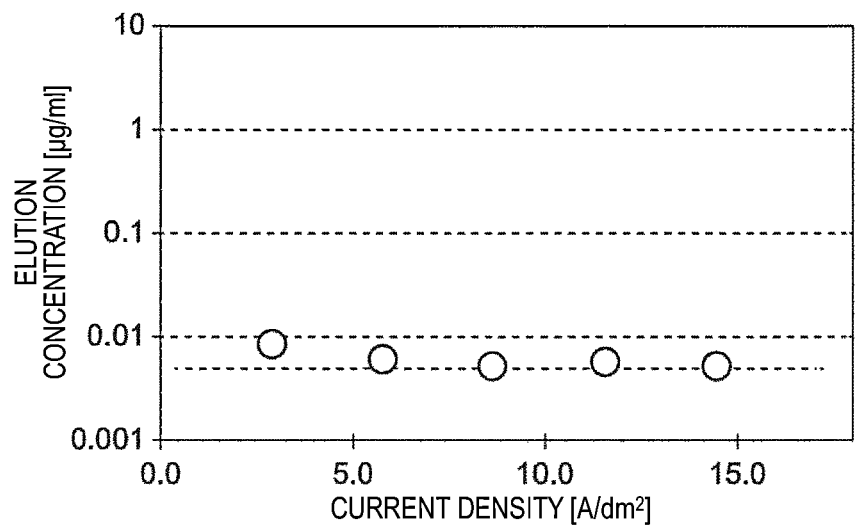
FIG. 11 is a graph of analysis results of the elution concentration of Pd in Example 4.

FIG. 10 is a graph of analysis results of the elution concentration of Ni in Example 4. FIG. 11 is a graph of analysis results of the elution concentration of Pd in Example 4. FIGS. 10 and 11 show that the elution concentrations of Pd and Ni were below the detection limit of the ICP-MS for Pd and Ni. This indicates that Pd and Ni are not eluted in Example 4.

Preferably, the current density ranges from 0.5 to 30 [A/dm$^2$]. More preferably, the current density ranges from 2.9 to 14.5 [A/dm$^2$].

Example 5

Example 5 is described below. In Example 5, the PdNi plating film 34 was formed by the above production method at different concentration ratios of Pd to Ni in the PdNi plating bath. In Example 5, the Pd concentration ratio ranged from 52% to 80%. The Pd concentration ratio is calculated using the formula Pd/(Pd+Ni). The Ni concentration ratio is calculated using the formula Ni/(Pd+Ni). In Example 5, the Pd concentration ratio of the PdNi plating film 34 formed by changing the Pd concentration ratio was analyzed to examine the effect of changing the Pd concentration ratio of the plating bath on the composition of the PdNi plating film 34.

Figure 12:
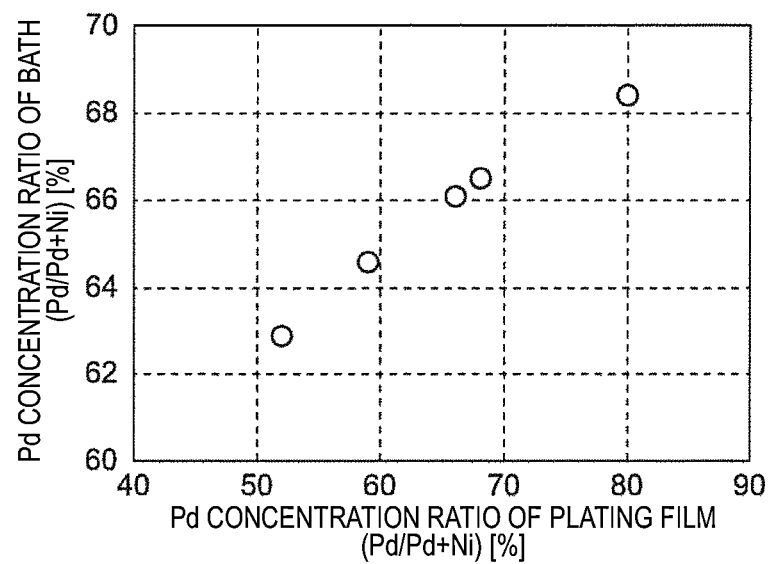
FIG. 12 is a graph of an example of the relationship between the Pd concentration ratio of a plating film and the Pd concentration ratio in Example 5.

FIG. 12 is a graph of an example of the relationship between the Pd concentration ratio of the plating film 34 and the Pd concentration ratio in Example 5. FIG. 12 shows that the concentration ratio of Pd to Ni in the plating bath in the formation of the PdNi plating film 34 can be controlled to change the component ratio of the PdNi plating film 34.

Figures 13, 14:
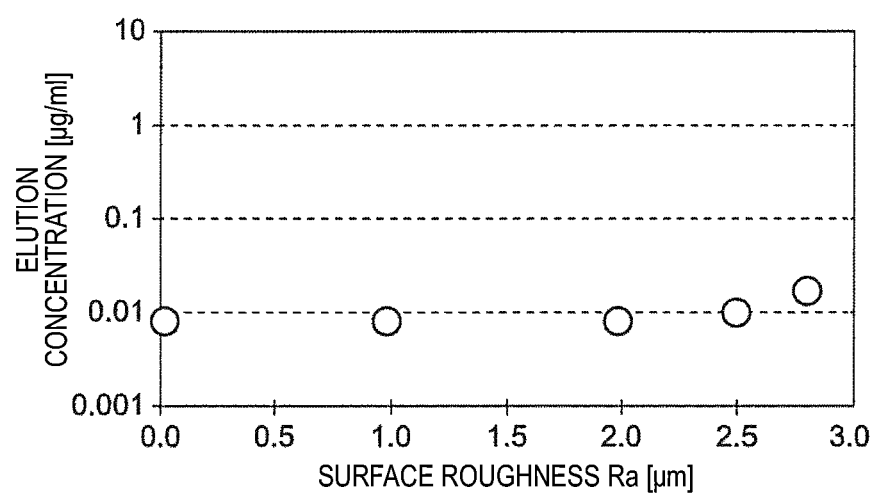
FIG. 13 is a table of analysis results of a Ni component in a surface layer of a PdNi plating film at each component ratio in Example 5.
FIG. 14 is a graph of analysis results of the elution concentration of Ni in Example 6.

In Example 5, each PdNi plating film 34 formed at the Pd concentration ratio shown in FIG. 12 was subjected to the XPS component analysis of the surface layer. FIG. 13 is a table of analysis results of the Ni component in the surface layer of the PdNi plating film 34 at each component ratio in Example 5. ND in FIG. 13 indicates that the value is below the detection limit of XPS.

FIG. 13 shows that the Ni ratio of the surface layer of the PdNi plating film 34 was ND at Pd:Ni ratios of 52:48, 58:42, 66:34, 68:32, and 80:20. This indicates that Ni is not detected in the surface layer of the PdNi plating film 34 in Example 5.

Example 6

Example 6 is described below. In Example 6, the filtration filter 10 was produced by the above production method at different surface roughnesses Ra of the PdNi plating film 34. The surface roughness Ra was changed by adjusting the pH value of the plating solution, the current density, the substrate base material, and the film thickness in the PdNi plating bath. In Example 6, the surface roughness Ra was 0.02, 0.94, or 1.98 μm. In Example 6, the filtration filter 10 was subjected to an elution test. In the elution test, a portion with a surface area of 1 cm 2 in the filtration filter 10 was immersed in 10 ml of PBS and was kept at 37° C. in an incubator for one week. In the same manner as in Examples 3 and 4, the elution concentration of Ni was analyzed with the ICP-MS (manufactured by Agilent Technologies).

FIG. 14 is a graph of analysis results of the elution concentration of Ni in Example 6. FIG. 14 shows that the elution concentration of Ni was below the detection limit of the ICP-MS for Ni. This indicates that Ni is not eluted in Example 6.

Preferably, the surface roughness Ra of the filtration filter 10 is 2.5 μm or less. More preferably, the surface roughness Ra of the filtration filter 10 is 1.98 μm or less.

The immersion of the PdNi plating film 34 in the aqueous acetic acid hydrogen peroxide dissolves and eliminates Ni on the surface layer and consequently increases the Pd content of the surface layer 21. The elution test of the PdNi plating film 34 in this state shows that the elution concentration of Ni is below the detection limit (0.01 μg/ml). At a surface roughness Ra of 2.5 μm or less, the immersion in the aqueous acetic acid hydrogen peroxide causes sufficient liquid exchange with the aqueous acetic acid hydrogen peroxide on the surface of the PdNi plating film 34, completely eliminates Ni from the surface layer 21, and increases the Pd content of the surface layer 21. At a surface roughness Ra of more than 2.5 μm, a portion of fine asperities of the surface layer 21 is not sufficiently covered with the aqueous acetic acid hydrogen peroxide, and liquid exchange is less likely to occur at the portion. It may be difficult to eliminate Ni and increase the Pd content at the portion of the surface layer 21. The elution test of the PdNi plating film 34 in this state shows that the Ni concentration was increased probably due to the elution of Ni remaining in the surface layer 21.

Example 7

Example 7 is described below. In Example 7, the filtration filter 10 was produced by the above production method at different immersion times of the PdNi plating film 34 in the aqueous acetic acid hydrogen peroxide. The PdNi plating film 34 in Example 7 has a Pd:Ni ratio of 9:1. In Example 7, the immersion time was 0 seconds, 10 seconds, 30 seconds, 1 minute, 5 minutes, 30 minutes, 1 hour, and 2 hours at room temperature. In Example 7, the aqueous acetic acid hydrogen peroxide is acetic acid 5%:hydrogen peroxide 5%:pure water 90%.

In Example 7, the components of the surface layer of the filtration filter 10 produced at different immersion times were analyzed by XPS. FIG. 15 is a table of analysis results of the Ni component in the surface layer of the filtration filter 10 in Example 7. FIG. 15 shows that an immersion time of 1 minute or more can result in the Ni content of 0% in the surface layer of the filtration filter 10.

Example 8

Example 8 is described below. In Example 8, the compositions of samples A1 and A2 of the filtration filter 10 produced by the above production method were examined.

In Example 8, TEM observation and EDX mapping were performed. The TEM observation was performed with an FE-TEM (JEOL Ltd.: JEM-F200). The TEM measurement conditions included accelerating voltage: 200 kV, focusing lens aperture: #2, and pretreatment: Pt coating. The EDX mapping was performed with Noran system 7 (Wakenyaku Co., Ltd.). The EDX measurement conditions included spot diameter: ϕ1.0 nm, time constant: Rate 1, and the number of scans: 100.

The sample A1 of the filtration filter 10 was prepared at a current density of 2.9 [A/dm$^2$]. The sample A2 was prepared at a current density of 14.5 [A/dm$^2$]. In the production of the filtration filter 10 of each of the samples A1 and A2, the immersion time of the PdNi plating film in the aqueous acetic acid hydrogen peroxide (acetic acid 5%:hydrogen peroxide 5%:pure water 90%) was 2 hours.

Figure 16A:
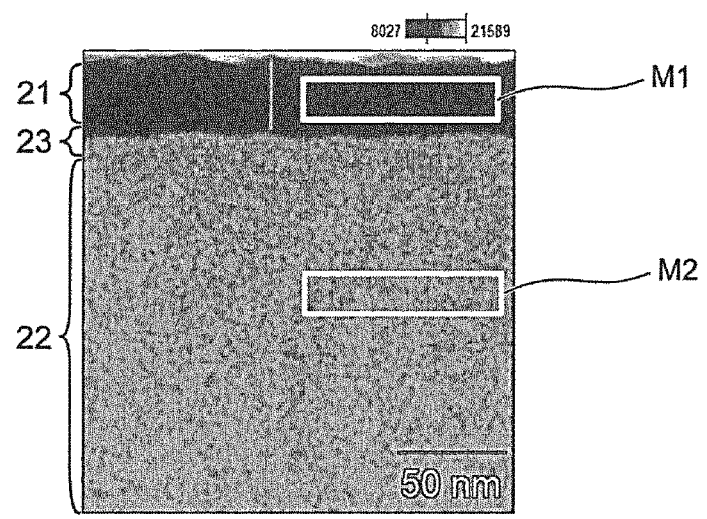
FIG. 16A is an EDX mapping of a sample A1 in Example 8.

FIG. 16A is an EDX mapping of the sample A1 in Example 8. In FIG. 16A, a portion M1 indicates a portion of the surface layer 21 of the sample A1, and a portion M2 indicates a portion of the base material of the sample A1. The intermediate layer 23 of the sample A1 in FIG. 16A is formed in a region at a distance of approximately 32 nm from the surface. The portion M2 of the base material 22 in FIG. 16A is a region at a distance of approximately 106 nm from the surface.

Figure 16B:
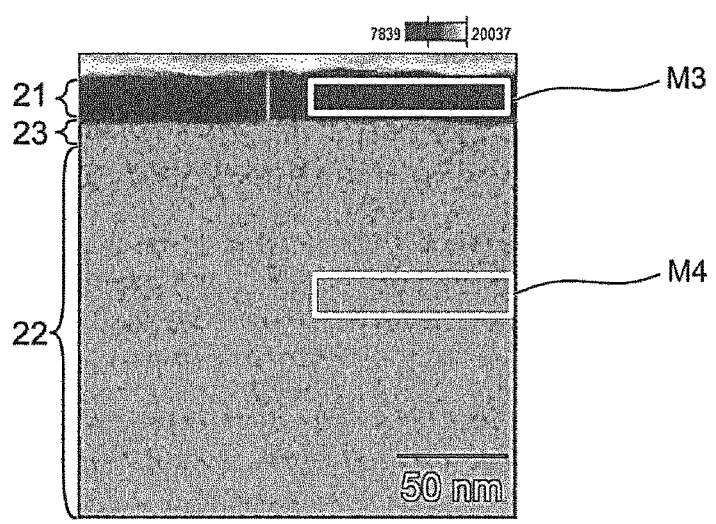
FIG. 16B is an EDX mapping of a sample A2 in Example 8.

FIG. 16B is an EDX mapping of the sample A2 in Example 8. In FIG. 16B, a portion M3 indicates a portion of the surface layer 21 of the sample A2, and a portion M4 indicates a portion of the base material 22 of the sample A2. The intermediate layer 23 of the sample A2 in FIG. 16B is formed in a region at a distance of approximately 22.5 nm from the surface. The portion M4 of the base material 22 in FIG. 16B was a region at a distance of approximately 97 nm from the surface.

The EDX quantitative analysis of the portion M1 in FIG. 16A showed Pd: 98.7%, Ni: 0.6%, and O: 0.7%. The EDX quantitative analysis of the portion M2 in FIG. 16A showed Pd: 81.6%, Ni: 18.4%, and O: 0%. It should be noted that values of less than 1% include noise.

The EDX quantitative analysis of the portion M3 in FIG. 16B showed Pd: 98.9%, Ni: 1.1%, and O: 0%. The EDX quantitative analysis of the portion M4 in FIG. 16B showed Pd: 76.6%, Ni: 23.4%, and O: 0%. It should be noted that values of less than 1% include noise.

FIGS. 16A and 16B show that Ni in the surface layer portion was eliminated in the samples A1 and A2 of Example 8. Thus, Ni in the surface layer portion was eliminated in the filtration filters 10 produced at a current density of 2.9 [A/dm$^2$] and at a current density of 14.5 [A/dm$^2$]. The difference in the Pd:Ni ratio between the portion M2 (base material portion) of the sample A1 and the portion M4 (base material portion) of the sample A2 is probably due to the difference in current density.

[Advantages]

The filtration filter 10 according to the first embodiment has the following advantages.

The filtration filter 10 includes the surface layer 21, the base material 22 inside the surface layer 21, and the intermediate layer 23 between the surface layer 21 and the base material 22. The surface layer 21 is composed mainly of Pd, the base material 22 is composed mainly of a PdNi alloy, and the intermediate layer 23 is composed mainly of a PdNi alloy in which the Pd:Ni ratio changes from the surface layer 21 side toward the base material 22 side. The filtration filter 10 with such a structure can have improved corrosion resistance.

To compare with the filtration filter 10, a filtration filter according to Comparative Example 1 is described below. In the filtration filter according to Comparative Example 1, a surface of a base material 122 formed of a non-precious metal is coated with a noble metal by plating to form a surface layer 121 of the noble metal on the surface of the base material 122 of the non-precious metal. In Comparative Example 1, the surface layer 121 is composed mainly of Pd, and the base material 122 is composed mainly of Ni.

Figure 17:
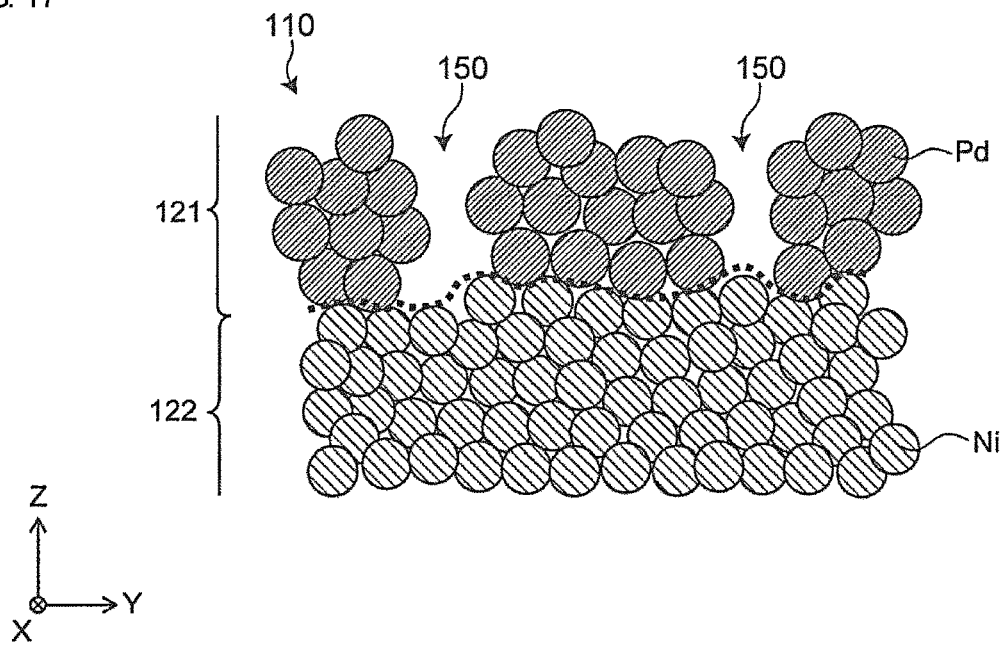
FIG. 17 is a schematic view of a portion of an example of a filtration filter according to Comparative Example 1.

FIG. 17 is a schematic view of a portion of an example of a filtration filter 110 according to Comparative Example 1. As illustrated in FIG. 17, in the filtration filter 110 according to Comparative Example 1, the surface layer 121 composed mainly of a noble metal Pd is formed on the base material 122 composed mainly of a non-precious metal Ni. Thus, a continuous interface is formed between the surface layer 121 and the base material 122. The plating forms defects 150 in the surface layer 121 due to impurities adhering to the surface of the base material 122 and/or due to surface roughness.

Thus, in the filtration filter 110 according to Comparative Example 1, a liquid, such as an electrolyte solution, easily comes into contact with the base material 122 through the defects 150 in the surface layer 121. This makes it difficult to prevent the base material 122 from being eluted through the defects 150.

The surface layer 121, the base material 122, and the electrolyte solution in contact with the interface between the surface layer 121 and the base material 122 tend to form a local cell, which causes an anodic reaction on the surface of the base material 122 made of the non-precious metal (Ni) and may result in corrosion of the base material 122. Furthermore, due to the continuous interface between the surface layer 121 and the base material 122, corrosion of the base material 122 spreads easily over the entire base material 122.

When the surface layer 121 is damaged and peeled off, the base material 122 is easily exposed and is easily eluted when coming into contact with the electrolyte solution.

On the other hand, in the filtration filter 10 according to the first embodiment, as illustrated in FIG. 3, the intermediate layer 23 is formed between the surface layer 21 and the base material 22. In the intermediate layer 23, the Pd:Ni ratio changes from the surface layer 21 side toward the base material 22 side. Thus, the interface between Pd and Ni is dispersed in the intermediate layer 23 of the filtration filter 10. This can prevent Ni from being eluted through defects in the surface layer 21 when the filtration filter 10 comes into contact with a liquid, such as an electrolyte solution.

Even when an electrolyte solution flows into the filtration filter 10 through defects in the surface layer 21, Pd and Ni are less likely to come into contact with each other via the electrolyte solution. Thus, a local cell is rarely formed at the interface between Pd and Ni, and Ni is less likely to be corroded. Furthermore, in the filtration filter 10, even when an electrolyte solution flows through defects in the surface layer 21, and Ni comes into contact with Pd via the electrolyte solution and is corroded, the dispersed interface between Pd and Ni possibly prevents the corrosion from spreading over the entire base material 22.

Even when the surface layer 21 is damaged and peeled off, only the intermediate layer 23 is exposed, and the base material 22 is rarely exposed. This can reduce the elution of the base material 22. Thus, in the filtration filter 10, the intermediate layer 23 formed between the surface layer 21 and the base material 22 can reduce the elution of the base material 22.

The ratio of Ni to Pd in the intermediate layer 23 increases with the depth in the depth direction D1 of the filtration filter 10. Such a structure can separate most of the Ni in the intermediate layer 23 from the surface layer 21 and reduce the elution and corrosion of Ni caused by contact with an electrolyte solution. This can further improve the corrosion resistance of the filtration filter 10.

The intermediate layer 23 has a larger thickness than the surface layer 21. Such a structure enables Ni to be further dispersed in the depth direction D1 of the filtration filter 10. Such a structure can also further separate the base material 22 from the surface layer 21 and can further reduce the elution and corrosion of the base material 22. This can further improve the corrosion resistance of the filtration filter 10.

The intermediate layer 23 is formed in a region with a depth of more than 10 nm and 30 nm or less from the surface of the filtration filter 10. More preferably, the intermediate layer 23 is formed in a region with a depth in the range of 20 to 30 nm from the surface of the filtration filter 10. The filtration filter 10 with such a structure can have further improved corrosion resistance.

Furthermore, the base material 22 is formed at a position deeper than the intermediate layer 23. In general, the permeation of an electrolyte solution decreases with increasing depth, and the chance of the electrolyte solution coming into contact with the base material decreases with increasing depth. The filtration filter 10 with such a structure can therefore have improved corrosion resistance.

The base material 22 has a Pd:Ni ratio of 80:20, and the intermediate layer 23 has a Pd:Ni ratio varying in the range of 100:0 to 80:20 from the surface layer 21 side toward the base material 22 side. The filtration filter 10 with such a structure can have further improved corrosion resistance.

Although the filtration filter 10 composed of Pd and the PdNi alloy is described in the first embodiment, the present invention is not limited to this embodiment. The filtration filter 10 may be made of a metal or alloy containing a noble metal other than Pd and a non-precious metal other than Ni.

Although the ratio of Ni to Pd in the intermediate layer 23 increases with the depth in the depth direction D1 of the filtration filter 10 in the present embodiment, the present invention is not limited to this embodiment. For example, the intermediate layer 23 may include a portion where the ratio of Ni to Pd in the PdNi alloy is constant and/or decreases. The filtration filter 10 with such a structure can also have improved corrosion resistance.

Although the intermediate layer 23 has a larger thickness than the surface layer 21 in the first embodiment, the present invention is not limited to this embodiment. For example, the intermediate layer 23 may have a thickness smaller than or equal to the thickness of the surface layer 21. The filtration filter 10 with such a structure can also have improved corrosion resistance.

Second Embodiment

In the second embodiment of the present invention, the filtration filter of the first embodiment is used as a mesh of a mesh nebulizer. Major differences between the second embodiment and the first embodiment are described below. In the second embodiment, the same or equivalent constituents as the constituents of the first embodiment are denoted by the same reference numerals and letters. The constituents described in the first embodiment are omitted in the second embodiment.

The second embodiment aims to improve the corrosion resistance of the mesh of the mesh nebulizer.

Figure 18:
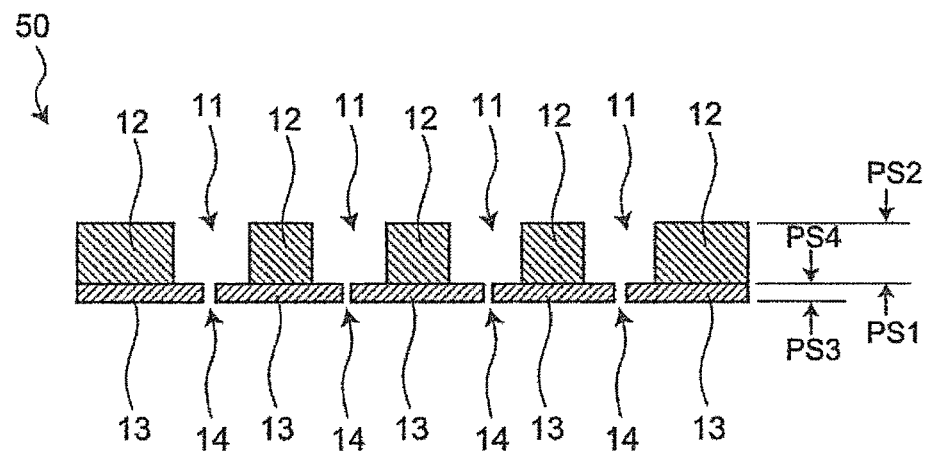
FIG. 18 is a schematic partial cross-sectional view of an example of a mesh according to a second embodiment of the present invention.

An example of the mesh of the second embodiment is described below with reference to FIG. 18. FIG. 18 is a schematic partial cross-sectional view of an example of a mesh 50 according to the second embodiment of the present invention. As illustrated in FIG. 18, the mesh 50 includes a first base portion 12 and a second base portion 13. First through-holes 11 and the first base portion 12 described in the second embodiment correspond to the through-holes 11 and the filter base portion 12 in the first embodiment.

The second base portion 13 is located on a first main surface PS1 side of the first base portion 12. The second base portion 13 is a plate-like member having a third main surface PS3 and a fourth main surface PS4 facing the third main surface PS3. The second base portion 13 has a smaller thickness than the first base portion 12.

The second base portion 13 and the first base portion 12 form a single body.

The second base portion 13 has a plurality of second through-holes 14. The second through-holes 14 are periodically arranged on the third main surface PS3 and the fourth main surface PS4 of the second base portion 13. More specifically, the second through-holes 14 are arranged in a matrix at regular intervals in the second base portion 13.

For example, the second through-holes 14 have a square lattice arrangement when viewed from the third main surface PS3 side (in the Z direction). The arrangement of the second through-holes 14 is not limited to the square lattice arrangement and may be a quasi-periodic arrangement or a periodic arrangement. The periodic arrangement may be a square or rectangular arrangement, such as a rectangular arrangement with intervals different in two array directions, a triangular lattice arrangement, or a regular triangular lattice arrangement. Alternatively, the second through-holes 14 may be any array of through-holes in the second base portion 13.

In the second embodiment, each of the second through-holes 14 has a square shape when viewed from the third main surface PS3 side (in the Z direction). The shape of the second through-holes 14 viewed from the third main surface PS3 side (in the Z direction) is not limited to square and may be rectangular, polygonal, circular, or elliptical.

In the second embodiment, the second through-holes 14 have a rectangular shape (cross-sectional shape) when projected onto a plane perpendicular to the third main surface PS3 of the second base portion 13. The cross-sectional shape of the second through-holes 14 is not limited to rectangular and may be a tapered shape, such as a parallelogram or trapezoid, a symmetric shape, or an asymmetric shape.

The second through-holes 14 have a smaller size than the first through-holes 11. When the second through-holes 14 have a square shape, the length of one side of the second through-holes 14 in the vertical direction (X direction) and the horizontal direction (Y direction) of the mesh 50 is smaller than the length of one side of the first through-holes 11. When the second through-holes 14 have a circular shape, the second through-holes 14 have a smaller diameter than the first through-holes 11.

The second through-holes 14 connect to the first through-holes 11. In other words, the second through-holes 14 communicate with the first through-holes 11.

Like the filtration filter 10 according to the first embodiment, the mesh 50 includes a surface layer 21, a base material 22 formed inside the surface layer 21, and an intermediate layer 23 formed between the surface layer 21 and the base material 22. The surface layer 21 of the mesh 50 is composed mainly of Pd. The base material 22 of the mesh 50 is composed mainly of a PdNi alloy. The intermediate layer 23 of the mesh 50 is composed mainly of a PdNi alloy in which the Pd:Ni ratio changes from the surface layer 21 side toward the base material 22 side.

[Example of Method for Producing Mesh]

An example of a method for producing the mesh 50 is described below with reference to FIGS. 19A to 19K. FIGS. 19A to 19K illustrate an example of a production process of the mesh 50 according to the second embodiment of the present invention.

Figure 19A:
FIG. 19A is a schematic view of an example of a production process of the mesh according to the second embodiment of the present invention.

As illustrated in FIG. 19A, a substrate 41 made of silicon or the like is prepared. The substrate 41 may be subjected to surface cleaning, for example.

Figure 19B:
FIG. 19B is a schematic view of an example of a production process of the mesh according to the second embodiment of the present invention.

As illustrated in FIG. 19B, a Cu film 42 500 nm in thickness is formed on the substrate 41. For example, the Cu film 42 is formed by sputtering with a sputter deposition apparatus. Alternatively, the Cu film 42 may be formed by vapor deposition with a vapor deposition apparatus. To improve the adhesion between the substrate 41 and the Cu film 42, a Ti film 50 nm in thickness may be formed between the substrate 41 and the Cu film 42.

Figure 19C:
FIG. 19C is a schematic view of an example of a production process of the mesh according to the second embodiment of the present invention.

As illustrated in FIG. 19C, a resist is applied to the Cu film 42 and is dried to form a resist film 43 2 μm in thickness. For example, a photosensitive positive liquid resist (Pfi-3A manufactured by Sumitomo Chemical Co., Ltd.) is applied to the Cu film 42 with a spin coater. The spin coater conditions include 1140 rpm and 30 seconds, for example. Next, the resist is heated and dried on a hot plate to form the resist film 43 2.0 μm in thickness. The hot plate conditions include a heating temperature of 90° C. and a heating time of 90 seconds, for example.

Figure 19D:
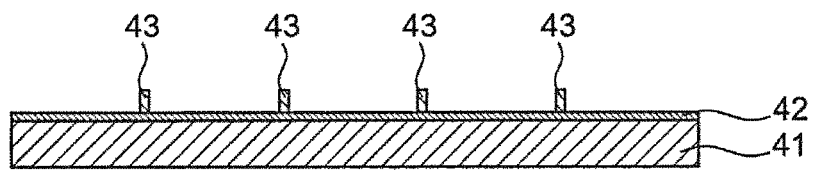
FIG. 19D is a schematic view of an example of a production process of the mesh according to the second embodiment of the present invention.

As illustrated in FIG. 19D, the resist film 43 is exposed to light and is developed to remove a portion of the resist film 43 corresponding to the second base portion 13. For example, an i-line stepper (Pfi-37A manufactured by Canon Inc.) is used as an exposure apparatus. Development is performed with a paddle developing apparatus. Tetramethylammonium hydroxide (TMAH) is used as a developer. Exposure to light and development are followed by washing with water and drying.

Figure 19E:
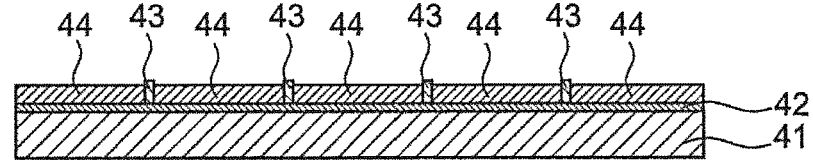
FIG. 19E is a schematic view of an example of a production process of the mesh according to the second embodiment of the present invention.

As illustrated in FIG. 19E, electroplating is performed in a PdNi plating bath with an electroplating apparatus. Thus, a PdNi plating film 44 is formed on the portion from which the resist film 43 has been removed. The electroplating conditions include a current density of 1 A/dm, an electric quantity of 4 AM, a pH of the plating solution of 7.5, and a plating thickness of 1.6 μm, for example.

Figure 19F:
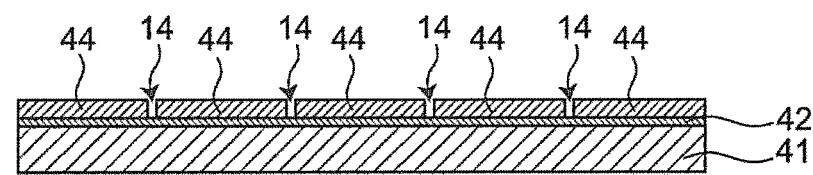
FIG. 19F is a schematic view of an example of a production process of the mesh according to the second embodiment of the present invention.

As illustrated in FIG. 19F, the resist film 43 is stripped with a stripping liquid NMP (N-methyl-2-pyrrolidone) in a resist stripping apparatus capable of high-pressure spray treatment. Subsequently, the PdNi plating film 44 is washed with IPA (isopropyl alcohol), is washed with water, and is dried.

Figure 19G:
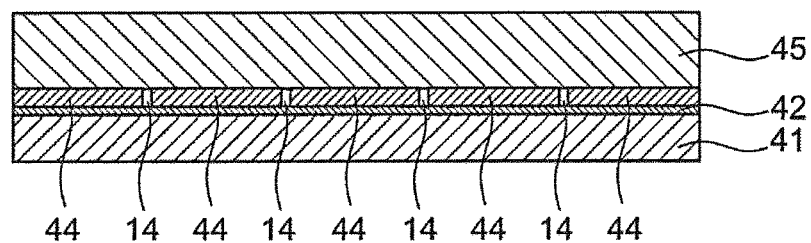
FIG. 19G is a schematic view of an example of a production process of the mesh according to the second embodiment of the present invention.

As illustrated in FIG. 19G, a dry film resist 45 is laminated to the PdNi plating film 44. The dry film resist 45 has a thickness of 50 μm. The upper and lower roll temperatures in the lamination are 100° C., and the feed rate is 0.4 m/s.

Figure 19H:
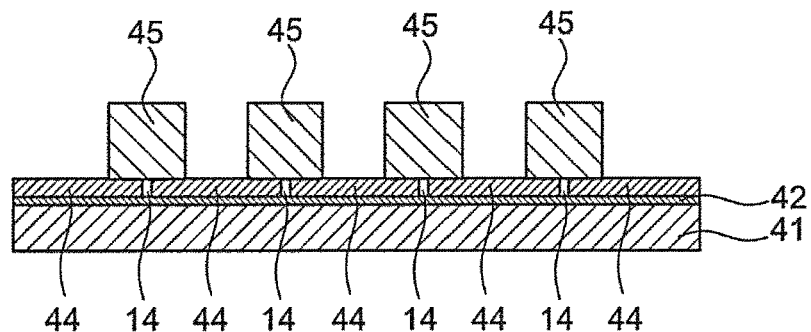
FIG. 19H is a schematic view of an example of a production process of the mesh according to the second embodiment of the present invention.

As illustrated in FIG. 19H, the dry film resist 45 is exposed to light and is developed to remove a portion of the dry film resist 45 corresponding to the first base portion 12. For example, the dry film resist 45 is exposed to light with an aligner and is developed by spray development. The developer is a 3% sodium carbonate solution.

Figure 19I:
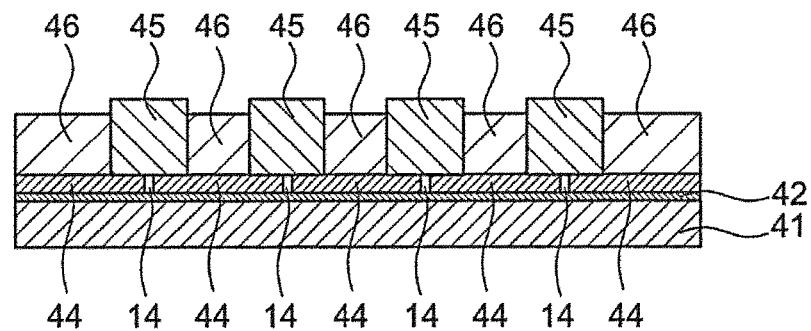
FIG. 19I is a schematic view of an example of a production process of the mesh according to the second embodiment of the present invention.

As illustrated in FIG. 19I, electroplating is performed in a PdNi plating bath with an electroplating apparatus. Thus, a PdNi plating film 46 is formed on the portion from which the dry film resist 45 has been removed. Immersion in 5% hydrochloric acid for 1 minute and washing with water were performed as plating pretreatment. After washing with water, PdNi electroplating was performed with an electroplating apparatus. The electroplating conditions include a current density of 1 A/dm$^2$, an electric quantity of 4 AM, a pH of the plating solution of 7.5, and a plating thickness of 1.6 μm, for example.

Figure 19J:
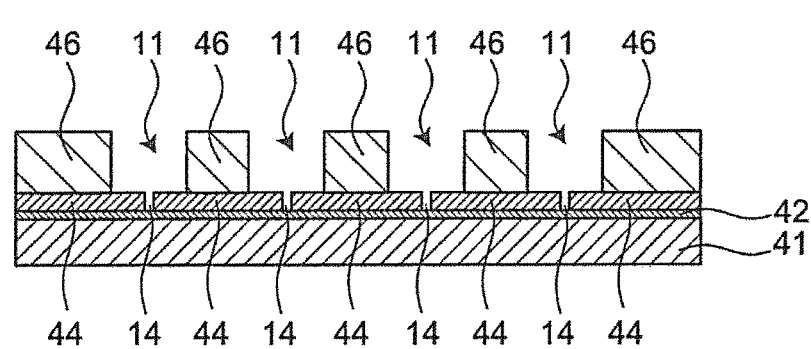
FIG. 19J is a schematic view of an example of a production process of the mesh according to the second embodiment of the present invention.

As illustrated in FIG. 19J, the resist film 45 is stripped with a stripping liquid NMP (N-methyl-2-pyrrolidone) in a resist stripping apparatus.

Figure 19K:
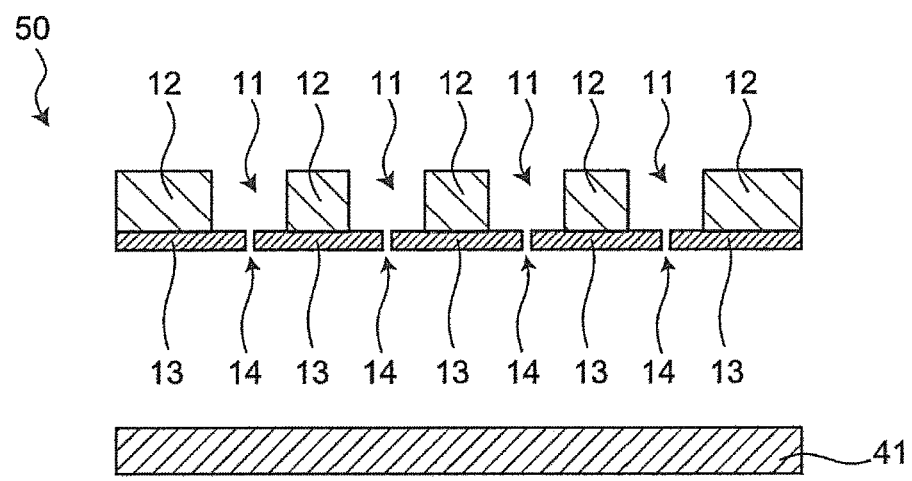
FIG. 19K is a schematic view of an example of a production process of the mesh according to the second embodiment of the present invention.

As illustrated in FIG. 19K, aqueous acetic acid hydrogen peroxide (acetic acid:hydrogen peroxide:water=5:5:90, room temperature) is adjusted as an etchant and as a liquid for dissolving and removing Ni from the surface layer of the PdNi plating films 44 and 46, and the Cu film 42 is etched by immersion treatment for 48 hours while stirring with a stirrer. Thus, the PdNi plating films 44 and 46 are removed from the substrate 41, and Ni in the surface layer of the PdNi plating films 44 and 46 is dissolved. Thus, the first base portion 12 and the second base portion 13 are formed.

The immersion treatment of the PdNi plating films 44 and 46 in the aqueous acetic acid hydrogen peroxide gradually dissolves Ni from the surface of the PdNi plating films 44 and 46 toward the inside. In the vicinity of the surfaces of the PdNi plating films 44 and 46, Ni in the PdNi plating films 44 and 46 easily comes into contact with the aqueous acetic acid hydrogen peroxide and is easily dissolved. However, it becomes more difficult for Ni in the PdNi plating films 44 and 46 at a deeper position to come into contact with the aqueous acetic acid hydrogen peroxide and to dissolve. Thus, the amount of dissolved Ni decreases gradually from the surface of the PdNi plating film 44 and 46 toward the inside.

Thus, in the vicinity of the surfaces of the first base portion 12 and the second base portion 13, the aqueous acetic acid hydrogen peroxide dissolves Ni, and the surface layer 21 composed mainly of Pd is formed. The amount of Ni dissolved in the aqueous acetic acid hydrogen peroxide decreases gradually from the surface layer 21 of the first base portion 12 and the second base portion 13 in the depth direction D1. The intermediate layer 23 thus formed is composed mainly of a PdNi alloy in which the Pd:Ni ratio changes. Thus, a portion of the PdNi plating films 44 and 46 in which Ni is not dissolved in the aqueous acetic acid hydrogen peroxide becomes the base material 22.

It is possible in this way to produce the mesh 50, which includes the surface layer 21 composed mainly of Pd, the base material 22 composed mainly of a PdNi alloy, and the intermediate layer 23 composed mainly of a PdNi alloy in which the Pd:Ni ratio changes formed between the surface layer 21 and the base material 22.

[Advantages]

The mesh 50 according to the second embodiment has the following advantages.

The mesh 50 includes the surface layer 21, the base material 22 formed inside the surface layer 21, and the intermediate layer 23 formed between the surface layer 21 and the base material 22. The surface layer 21 is composed mainly of Pd, the base material 22 is composed mainly of a PdNi alloy, and the intermediate layer 23 is composed mainly of a PdNi alloy in which the Pd:Ni ratio changes from the surface layer 21 side toward the base material 22 side. The mesh 50 with such a structure can have improved corrosion resistance.

Although the mesh 50 includes the first base portion 12 and the second base portion 13 in the second embodiment, the present invention is not limited to this embodiment. It is only necessary that the mesh 50 includes the surface layer 21, the base material 22, and the intermediate layer 23. The mesh 50 may include no second base portion 13.

Although the present invention has been fully described in connection with preferred embodiments with reference to the accompanying drawings, various variations and modifications will be apparent to those skilled in the art. It is to be understood that such variations and modifications are within the scope of the present invention defined by the appended claims as long as they do not depart from the scope of the present invention.

The filtration filter according to the present invention is useful in filtering an object to be filtered in a liquid.

REFERENCE SIGNS LIST 10 filtration filter
11 through-hole (first through-hole)
12 filter base portion (first base portion)
13 second base portion
14 second through-hole
21 surface layer
22 base material
23 intermediate layer
31 substrate
32 Cu film
33 resist film
34 PdNi plating film
41 substrate
42 Cu film
43 resist film
44 PdNi plating film
45 dry film resist
46 PdNi plating film
50 mesh

The invention claimed is:

1. A filtration filter comprising:
a surface layer composed mainly of Pd;
a base material composed mainly of a PdNi alloy; and
an intermediate layer between the surface layer and the base material, wherein the intermediate layer is composed mainly of a PdNi alloy in which a Pd:Ni ratio changes from a surface layer side toward a base material side.

2. The filtration filter according to claim 1, wherein a ratio of Ni to Pd in the intermediate layer increases from the surface layer side toward the base material side.

3. The filtration filter according to claim 2, wherein the intermediate layer has a larger thickness than the surface layer.

4. The filtration filter according to claim 3, wherein the intermediate layer is in a region with a depth of more than 10 nm and 35 nm or less from a surface of the filtration filter.

5. The filtration filter according to claim 1, wherein the intermediate layer has a larger thickness than the surface layer.

6. The filtration filter according to claim 5, wherein the intermediate layer is in a region with a depth of more than 10 nm and 35 nm or less from a surface of the filtration filter.

7. The filtration filter according to claim 1, wherein
the base material has a Pd:Ni ratio of 80:20, and
the intermediate layer has a Pd:Ni ratio varying in a range of 100:0 to 80:20 from the surface layer side toward the base material side.

8. The filtration filter according to claim 1, wherein
the base material has a Pd:Ni ratio in a range of 75:25 to 85:15, and
the intermediate layer has a Pd:Ni ratio varying in a range of 100:0 to 75:25 from the surface layer side toward the base material side.

9. The filtration filter according to claim 1, wherein the surface layer has a Pd:Ni ratio of 100:0.

10. The filtration filter according to claim 1, wherein the base material has a larger thickness than the surface layer and the intermediate layer.

11. The filtration filter according to claim 1, wherein the base material includes a first base portion and a second base portion.

12. The filtration filter according to claim 11, wherein the second base portion has a smaller thickness than the first base portion.

13. The filtration filter according to claim 11, wherein the first base portion defines a plurality of first through-holes, and the second base portion defines a plurality of second through-holes having a smaller size than the plurality of first through-holes.

14. The filtration filter according to claim 13, wherein the plurality of second through-holes connect to the plurality of first through-holes.

* * * * *